(12) United States Patent
Maxwell et al.

(10) Patent No.: US 12,011,201 B2
(45) Date of Patent: Jun. 18, 2024

(54) BONE SCREWS

(71) Applicant: Choice Spine, LLC, Knoxville, TN (US)

(72) Inventors: Keith Melvin Maxwell, Hendersonville, NC (US); David Wiles, Chattanooga, TN (US); Julian Price, Bogart, GA (US); Justin Splane, Knoxville, TN (US); Alicia Henderson, Knoxville, TN (US); Jayden Garfield, Knoxville, TN (US); Matthew B. Kubo, Knoxville, TN (US)

(73) Assignee: Choice Spine, LLC, Knoxville, TN (US)

( * ) Notice: Subject to any disclaimer, the term of this patent is extended or adjusted under 35 U.S.C. 154(b) by 0 days.

(21) Appl. No.: 17/866,798

(22) Filed: Jul. 18, 2022

(65) Prior Publication Data

US 2023/0025644 A1 Jan. 26, 2023

Related U.S. Application Data

(60) Provisional application No. 63/224,017, filed on Jul. 21, 2021.

(51) Int. Cl.
*A61B 17/86* (2006.01)

(52) U.S. Cl.
CPC ........ *A61B 17/8615* (2013.01); *A61B 17/864* (2013.01); *A61B 17/866* (2013.01)

(58) Field of Classification Search
CPC ........................................... A61B 17/84–8695
See application file for complete search history.

(56) References Cited

U.S. PATENT DOCUMENTS

| 5,735,898 | A  | * | 4/1998 | Brånemark | A61B 17/8625 |
| | | | | | 606/317 |
| 6,022,352 | A  | * | 2/2000 | Vandewalle | A61B 17/746 |
| | | | | | 606/65 |
| 10,631,905 | B2 | * | 4/2020 | Asfora | A61B 17/8625 |
| 2004/0015172 | A1 | * | 1/2004 | Biedermann | A61B 17/863 |
| | | | | | 606/328 |

(Continued)

OTHER PUBLICATIONS

International Searching Authority, Patent Cooperation Treaty, Notification of Transmittal of the International Search Report and The Written Opinion of the International Searching Authority, or the Declaration (PCT Rule 44.1), PCT/US22/37563, ISA/US Alexandria, Virginia, USA, Kari Rodriquez, dated Oct. 25, 2022.

(Continued)

*Primary Examiner* — Eduardo C Robert
*Assistant Examiner* — Steven J Cotroneo
(74) *Attorney, Agent, or Firm* — Luedeka Neely, P.C.

(57) ABSTRACT

A bone screw includes a screw body having a head at one end of the screw and a tip at an opposite end of the screw; head threads directly attached to the screw body and continuous around the head of the screw; tip threads directly attached to the screw body and continuous around the tip of the screw; and overhanging thread portions between the head threads and the tip threads, the overhanging thread portions spaced apart, with unthreaded channels between the overhanging thread portions and the overhanging thread portions overhanging a portion of the unthreaded channels.

11 Claims, 9 Drawing Sheets

(56) References Cited

U.S. PATENT DOCUMENTS

| | | | |
|---|---|---|---|
| 2006/0241623 A1* | 10/2006 | Lim | A61B 17/8625 606/265 |
| 2015/0272646 A1* | 10/2015 | Russell | A61B 17/8841 606/93 |
| 2016/0220291 A1* | 8/2016 | Russell | A61B 17/8605 |
| 2019/0343565 A1* | 11/2019 | Tempco | A61B 17/863 |
| 2020/0107868 A1 | 4/2020 | Kolb | |
| 2020/0163704 A1 | 5/2020 | Shmueli | |
| 2021/0153911 A1* | 5/2021 | Stuart | A61B 17/869 |

OTHER PUBLICATIONS

Patent Treaty Cooperation, International Bureau, International Preliminary Report on Patentability, Form PCT/IB/326 for PCT Application PCT/US2022/037563, International filing Date Jul. 19, 2022, dated Feb. 1, 2024.

* cited by examiner

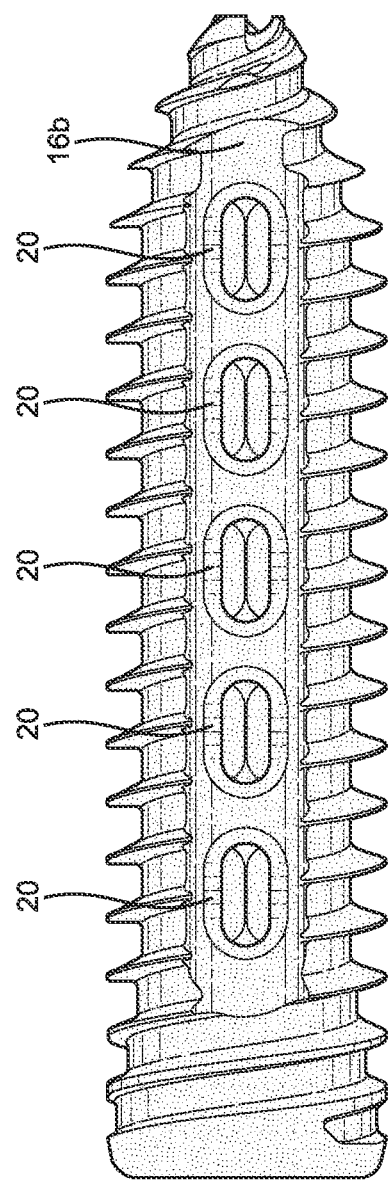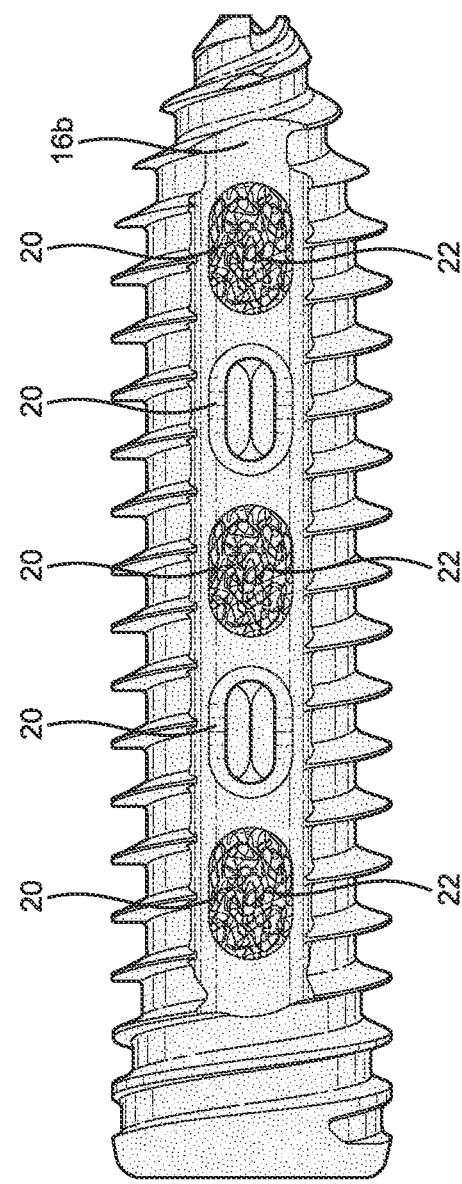

BONE SCREWS

FIELD

The present disclosure relates to bone screws. More particularly, the disclosure relates to bone screws of improved manufacture, structure and aesthetics, and particularly configured for promoting bone growth to and through the screw.

BACKGROUND

Improvement is desired in the provision of bone screws. In particular, improvement is desired for the structure and manufacture of bone screws configured for promoting bone growth to and through the screw.

In addition, a need exists for such improved bones screws that are particularly configured for use in fixation of the sacroiliac (SI) joint. The SI joint is located in the pelvis. It links the iliac bone (pelvis) to the sacrum (lowest part of the spine above the tailbone).

SUMMARY

The disclosure relates to a bone screw configured for promoting bone growth to and through the screw.

In one aspect, a screw according to the disclosure includes a screw body having a head at one end of the screw and a tip at an opposite end of the screw; head threads directly attached to the screw body and continuous around the head of the screw; tip threads directly attached to the screw body and continuous around the tip of the screw; and overhanging thread portions between the head threads and the tip threads, the overhanging thread portions being spaced apart, with unthreaded channels between the overhanging thread portions and the overhanging thread portions overhanging a portion of the unthreaded channels.

In another aspect, the disclosure provides method of manufacturing a bone screw by 3-D printing to provide the bone screw configured to have a screw body having a head at one end of the screw and a tip at an opposite end of the screw; head threads directly attached to the screw body and continuous around the head of the screw; tip threads directly attached to the screw body and continuous around the tip of the screw; and overhanging thread portions between the head threads and the tip threads, the overhanging thread portions being spaced apart, with unthreaded channels between the overhanging thread portions and the overhanging thread portions overhanging a portion of the unthreaded channels.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein:

FIGS. 11-14 show window features of the bone screw.

DETAILED DESCRIPTION

With reference to the drawings, there is shown a bone screw 10 of improved construction and aesthetics according to the disclosure. The bone screw 10 is particularly configured for promoting bone growth to and through the screw. The bone screw 10 is particularly suitable for installation at the sacroiliac joint of a patient but may be used for other sites of the body.

The bone screw 10 is preferably manufactured by 3-D printing and is most preferably printed using 3-D printing techniques know as Direct Metal Laser Sintering (DMLS) techniques using Titanium Alloy (Ti-6A1-4V). One significant advantage of manufacture of the bone screw 10 by DMLS is that the bone screw 10 may be used in surgeries as printed and requires no post-printing machining. This enables reduced manufacturing costs and enables more consistent quality with reduced labor requirements.

Manufacture of the bone screw 10 by DMLS techniques also advantageously enables unique structures, shapes, and other features to be provided on the bone screw 10. For example, the screw 10 has a bone receptive rugous outer surface and has porous structures on the surface of the screw 10 and internal features of the screw 10 as described herein.

Figure 1:
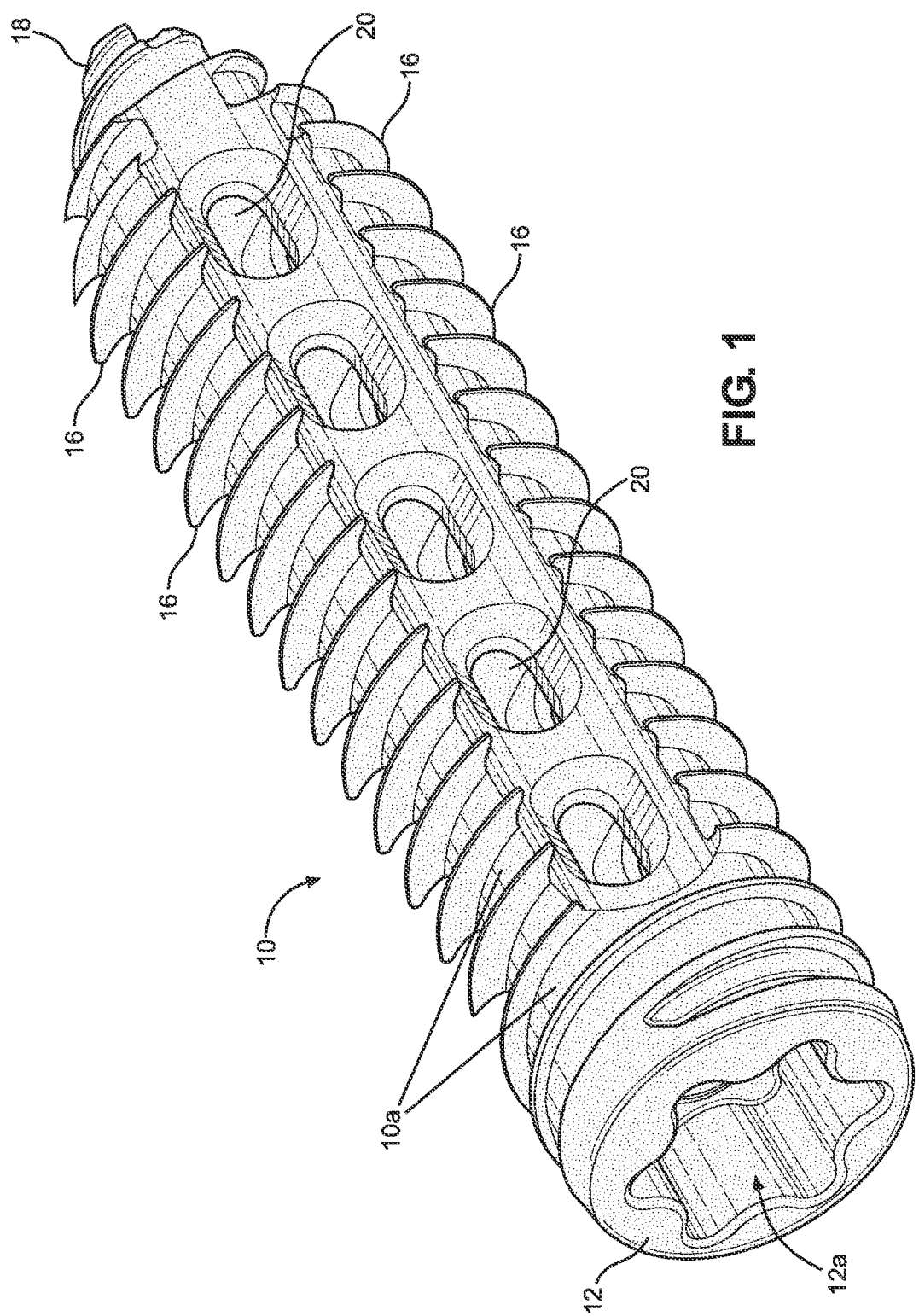
FIG. 1 is a perspective view of a bone screw according to the disclosure.
Figure 2:
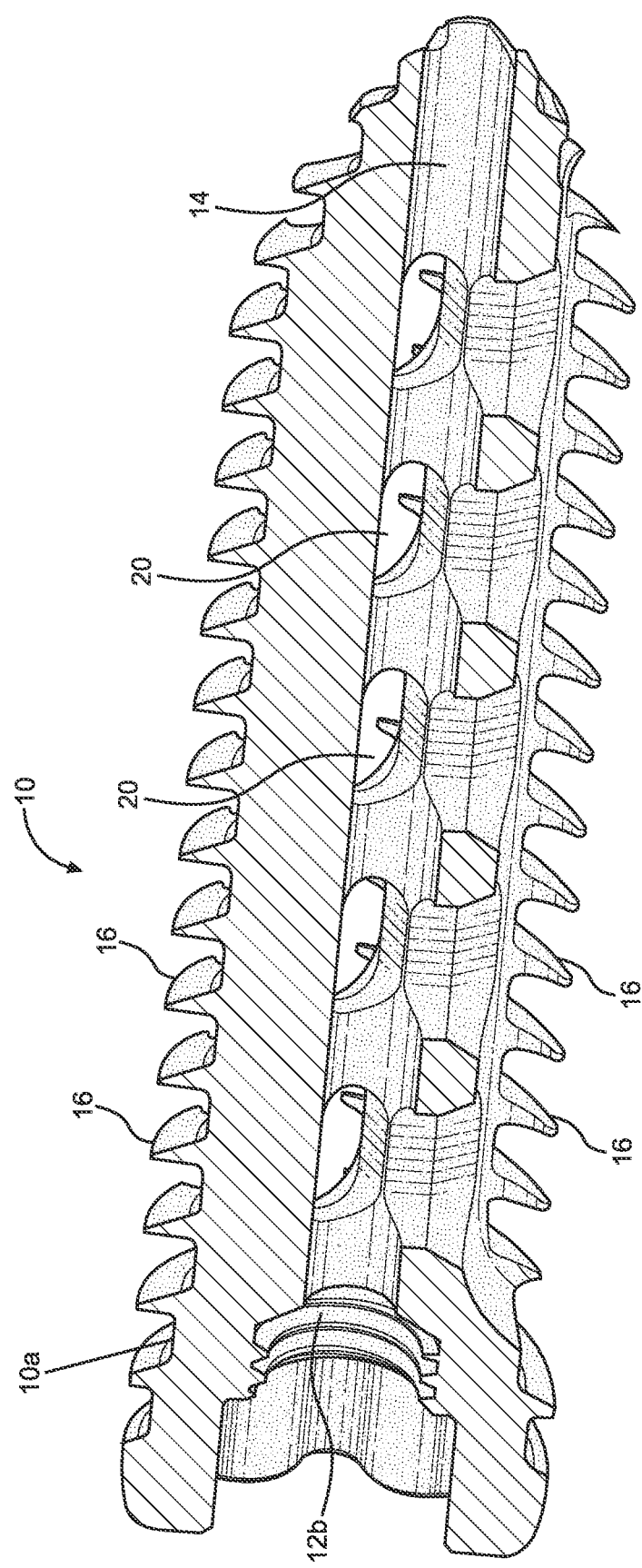
FIG. 2 is a cross-sectional view thereof.
Figure 3:
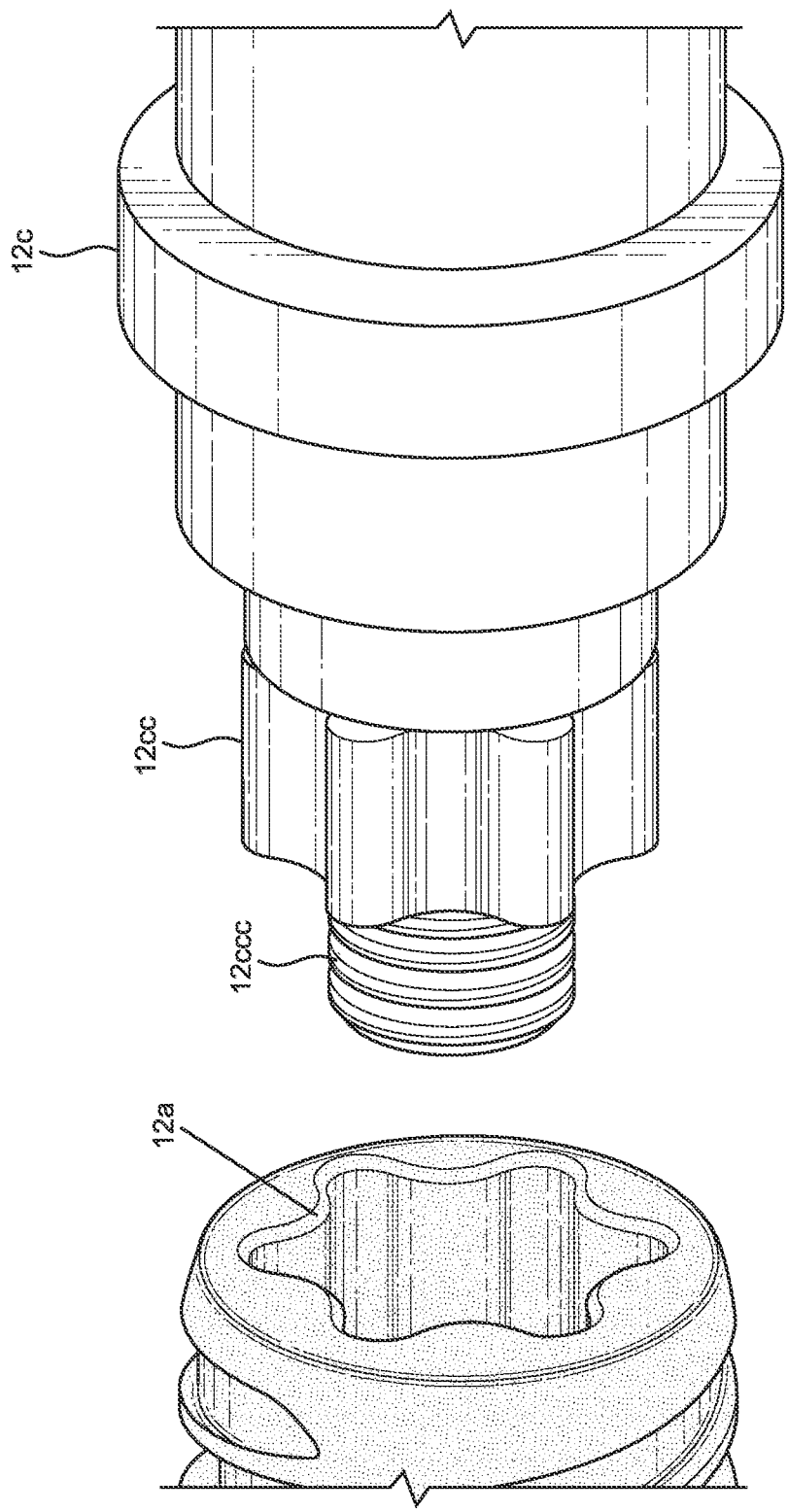
FIG. 3 shows a head of the screw and a drive configured to drive the screw.
Figure 4:
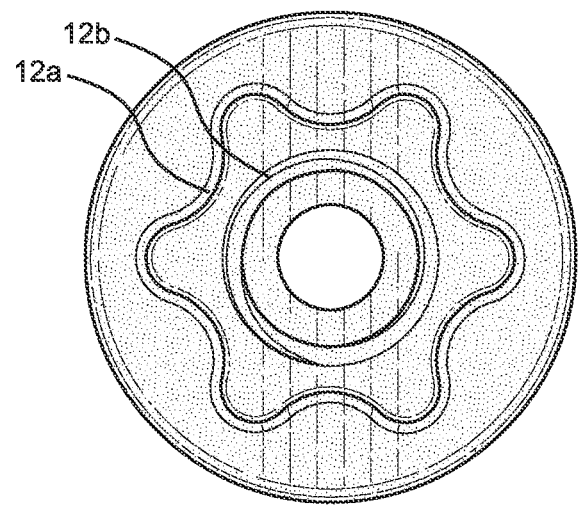
FIG. 4 is the head end view of the bone screw.
Figure 5:
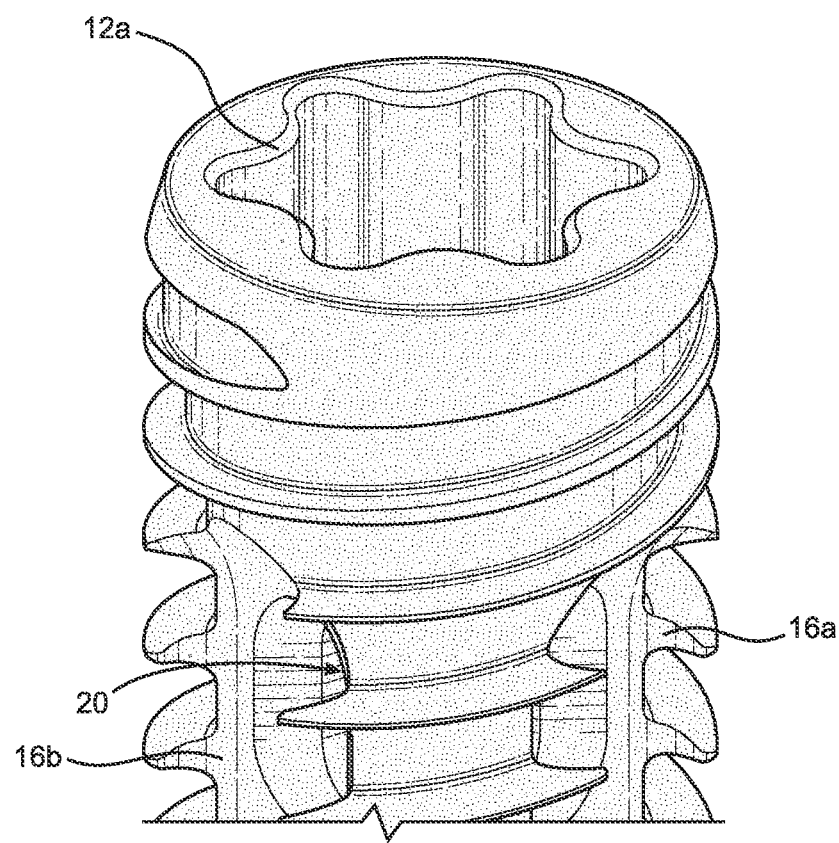
FIG. 5 is a closeup perspective view of a head of the bone screw.
Figure 6:
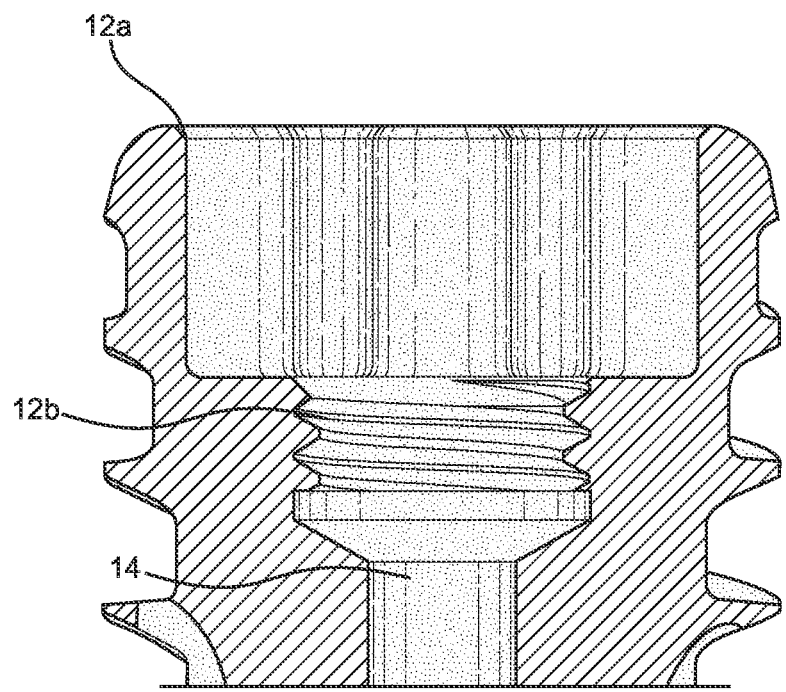
FIG. 6 is a cross-sectional view of the head.
Figure 7:
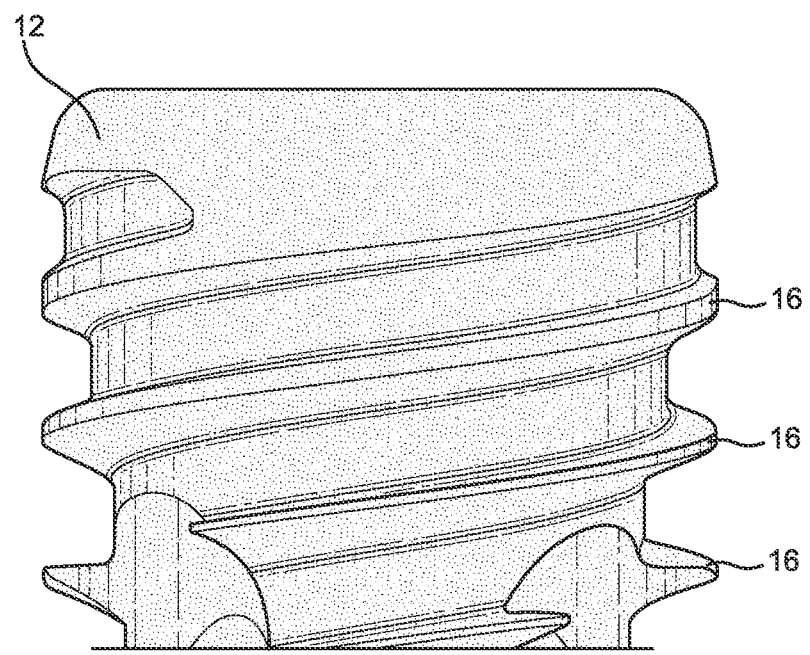
FIG. 7 is a closeup view of the side of the head.
Figure 8:
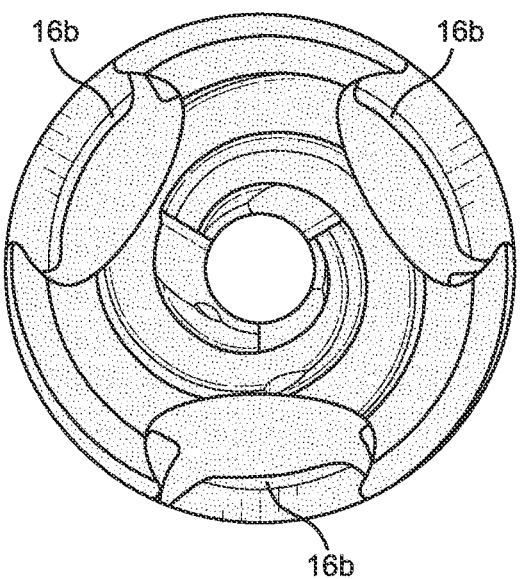
FIG. 8 is a tip end view of the bone screw.

Manufacture of the screw 10 by DMLS has been observed to provide the bone screw 10 with a roughened surface which is believed to be advantageous for promoting bone growth. For example, as shown in FIG. 1, the screw 10 as formed by DMLS has a body 10a with an exterior roughened surface over the entirety of the screw that is configured to be more receptive to bone growth onto the surface than the surface of conventional titanium screws that have a relatively smooth surface.

The manufacturing method also facilitates formation of a head 12 of the screw 10 that facilitate interaction of the bone screw 10 with insertion tools. As shown, the head 12 is configured to include insertion features such as a large internal or recessed complex geometric shaped drive 12a, such as a T-50 drive or hexalobe-shaped drive, and internal threads 12b within the head 12 and below the drive 12a. In this manner, a compatibly configured screw inserter 12c such as shown having a T-50 drive 12cc and threaded tip 12ccc may be utilized for more secure connection between the inserter and the bone screw 10. The drive 12cc fits the drive 12a and the threaded tip 12ccc threads into the internal threads 12b. The bone screw 10 is also formed to include a cannula 14 for receiving a guide wire if desired.

The screw 10 has a triangular cross-section and is formed to include threads 16 configured for screwing into a bone. An upper portion of the threads 16 continue their runout onto the head 12 for aiding in installation of the screw 10, and in providing a tactile feel to the physician when seating the screw 10. Also, the threads 16 blunt towards the head 12 to help prevent soft tissue damage if the head 12 of the screw 10 is left proud.

Another feature of the bone screw 10 enabled by the manufacturing method is the provision of overhanging thread portions 16a. For example, as shown, the threads 16 are continuous around the body 10a at the head 12 and a tip 18. However, in between the head 12 and the tip 18 the threads 16 are not continuous and have exposed ends which provide the overhanging thread portions 16a.

As seen, the overhanging thread portions 16a are spaced-apart, with unthreaded channels 16b between the sets of overhanging thread portions 16a. The overhanging thread portions 16a as shown are provided in three radially spaced apart sets but may be in other spacings. The overhanging thread portions 16a extend above or overhanging a portion of the unthreaded channels 16b. The combination of the overhanging thread portions 16a and the unthreaded channels 16b provides three fluted channels that are configured for improvement of bone collection onto the screw 10 during installation and subsequent growth of bone onto the screw 10.

Figure 9:
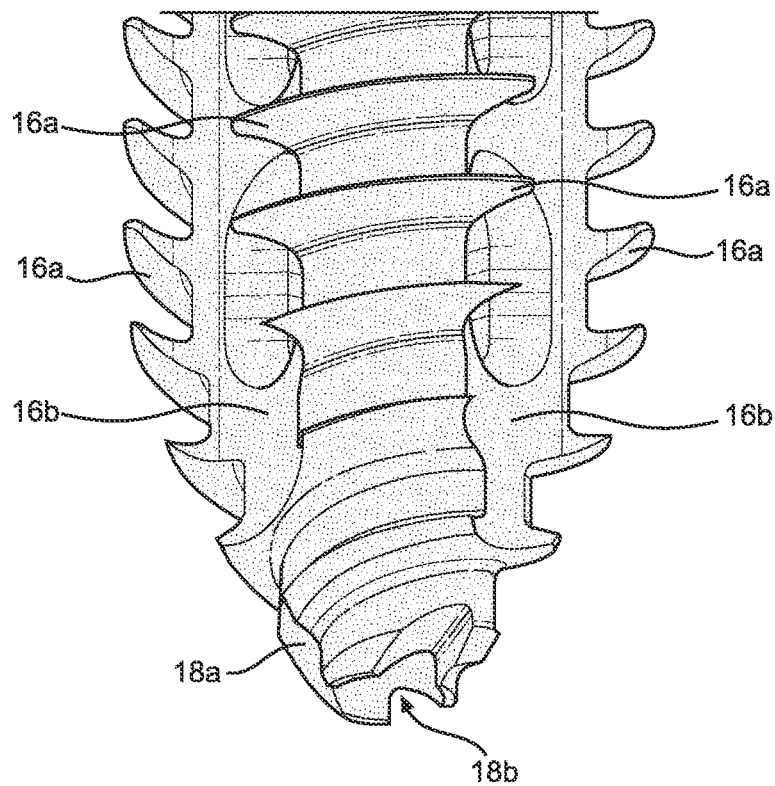
FIG. 9 is a closeup side view of the tip of the bone screw.
Figure 10:
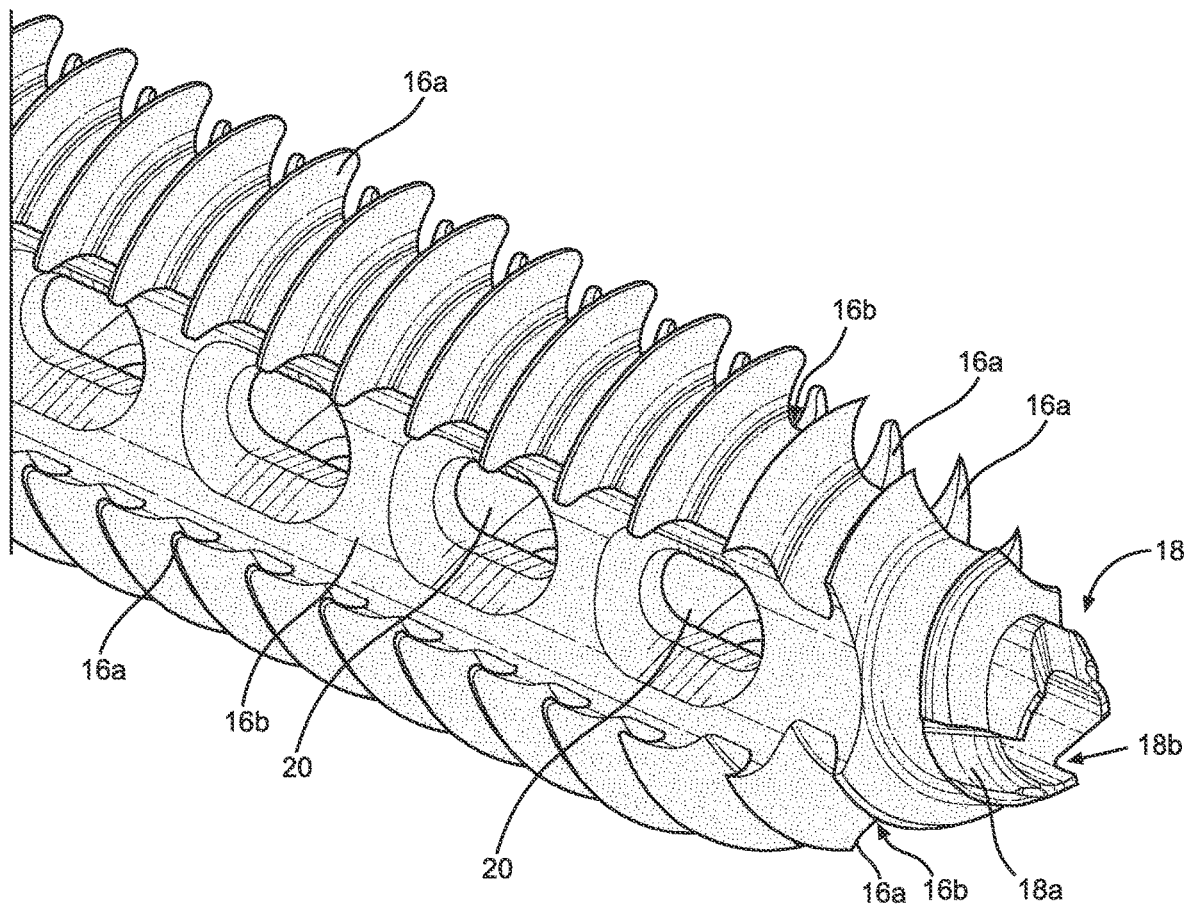
FIG. 10 is a closeup perspective view of the tip of the bone screw.

The tip 18 is configured as a cutting tip with cutting flutes 18a defining cutouts 18b (FIG. 9). During installation of the screw 10 into the bone, as bone is cut the channels 16b fill with cut bone, which aids in fusion of the bone to the screw 10 as the bone heals.

Another feature of the screw 10 is the provision of openings or windows 20 along the length of the bone screw 10 and located in the unthreaded channels 16b between the sets of overhanging thread portions 16a. The windows 20 provide access for bone graft to feed into interior portions of the screw 10 and provide zones of continuous porosity and permeability. The windows 20 are provided to facilitate the growth of bone through the screw 10 and along the surfaces of the screw 10.

Each of the windows 20 of one of the unthreaded channels 16b is preferably aligned with correspondingly located windows 20 of the other unthreaded channels 16b. As depicted, the windows 20 are desirably oblong in shape to provide open areas while retaining strength if the screw 10. However, the windows 20 may be of other shape. The windows 20 may be of uniform or non-uniform dimension. The dimensions of the windows 20 desirably correspond to and change to correspond to changes in the diameter and length of the screw 10 to preserve the structural strength of the screw 10 while still maximizing the surface area of the windows 20 for promoting bone growth to and through the screw 10.

Figures 11, 12:
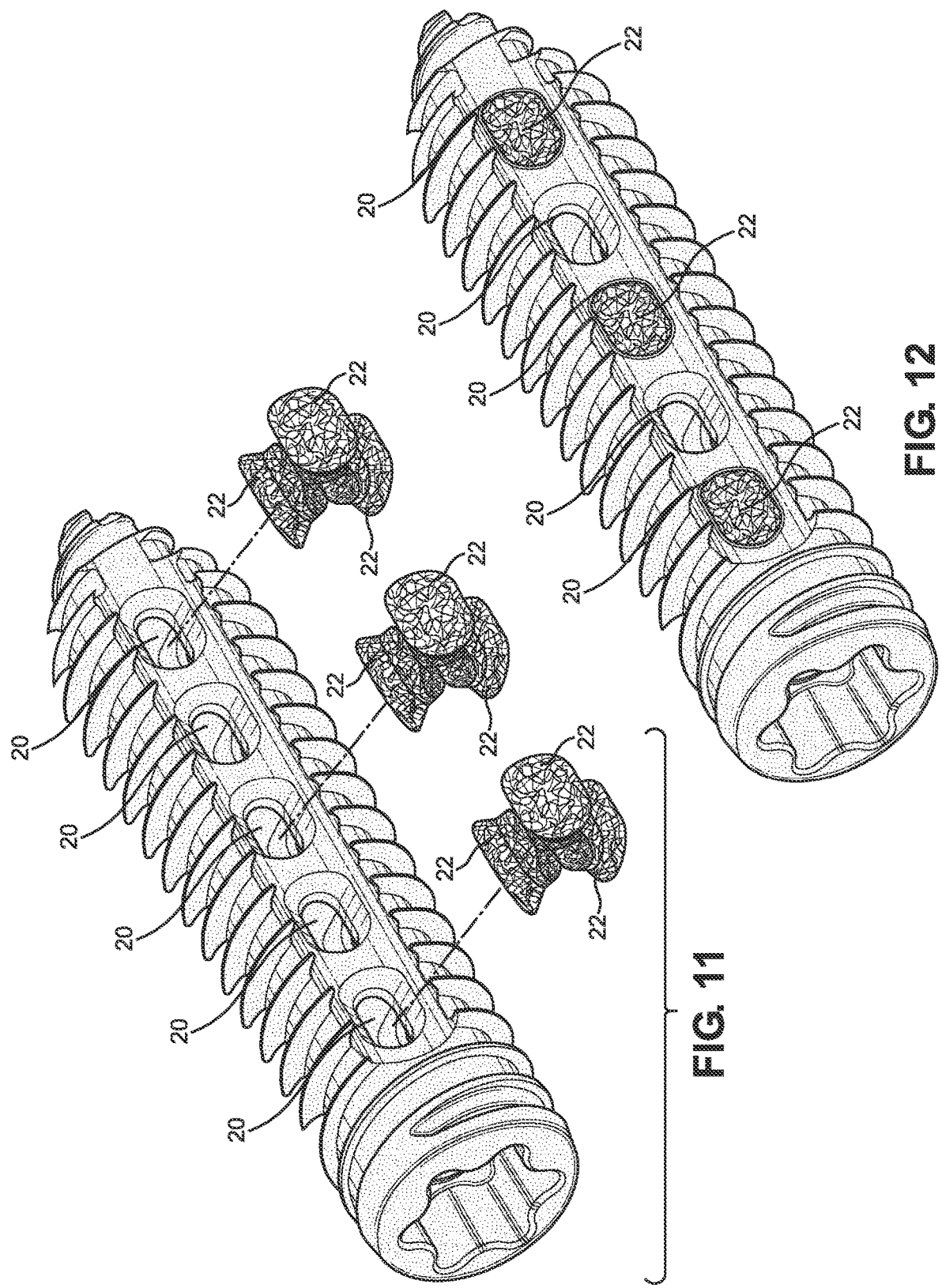

One or more of the windows 20 may be formed to include a permeable and porous fill 22 occupying the window 20. The fill 22 is formed during the printing of the screw 10 by DMLS and is integrally formed as part of the structure of the window as it is printed as shown in FIG. 12. As shown, the screw 10 may be formed with all of the windows 20 open, or a combination of some of the windows 20 open and some having the fill 22, or even all having the fill 22.

The bone screw 10 may be provided in various dimensions and without the windows. It will be appreciated that the rough surface of the DMLS printed screw in of itself provides a surface that is favorable to promote bone growth to the screw. However, the use of the windows 20 as described is preferred.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

The invention claimed is:

1. A bone screw, comprising:
a screw body having a length with a head at one end of the screw and a tip at an opposite end of the screw, the screw body having an exterior roughened surface over the entirety thereof that is configured to be more receptive to bone growth than a smooth exterior surface;
head threads directly attached to the screw body and continuous around the head of the screw;
tip threads directly attached to the screw body and continuous around the tip of the screw; and
overhanging thread portions between the head threads and the tip threads, the overhanging thread portions being spaced apart, with radially spaced apart sets of unthreaded channels aligned with the length of the screw body between the overhanging thread portions and the overhanging thread portions overhanging a portion of the unthreaded channels, the overhanging thread portions and the radially spaced apart sets of unthreaded channels providing radially spaced apart fluted channels, with one or more windows in each of the fluted channels, each of the windows of each of the fluted channels being aligned with correspondingly located windows of the other unthreaded channels and one or more of the windows includes a permeable and porous fill occupying the window.

2. The bone screw of claim 1, wherein the bone screw has a triangular cross-section and the unthreaded channels comprise three of the radially spaced apart sets of unthreaded channels providing the triangular cross-section.

3. The bone screw of claim 1, wherein the head includes an internal complex geometric shaped drive and internal threads within the head.

4. The bone screw of claim 1, wherein the tip is configured as a cutting tip formed to have cutting flutes and large channel cutouts.

5. The bone screw of claim 1, further comprising a cannula extending from the head to the tip.

6. A method of making a bone screw, comprising the steps of:
manufacturing a bone screw by 3-D printing to provide the bone screw configured to have a screw body having a length with a head at one end of the screw and a tip at an opposite end of the screw, the screw body having an exterior roughened surface over the entirety thereof that is configured to be more receptive to bone growth than a smooth exterior surface; head threads directly attached to the screw body and continuous around the head of the screw; tip threads directly attached to the screw body and continuous around the tip of the screw; and overhanging thread portions between the head threads and the tip threads, the overhanging thread portions being spaced apart, with radially spaced apart sets of unthreaded channels aligned with the length of the screw body between the overhanging thread portions and the overhanging thread portions overhanging a portion of the unthreaded channels, the overhanging thread portions and the radially spaced apart sets of unthreaded channels providing radially spaced apart fluted channels, with one or more windows in each of the fluted channels, each of the windows of each of the fluted channels being aligned with correspondingly located windows of the other unthreaded channels and one or more of the windows includes a permeable and porous fill occupying the window.

7. The method of claim 6, wherein the head is printed to include an internal complex geometric shaped drive and internal threads within the head.

8. The method of claim 6, wherein the tip is printed to have cutting flutes and large channel cutouts.

9. The method of claim 6, wherein the 3-D printing comprises Direct Metal Laser Sintering.

10. The method of claim 9, wherein the screw is printed using a titanium alloy.

11. The method of claim 6, wherein the bone screw is suitable for use as an implant in a human with no post-printing machining.

\* \* \* \* \*